US00PP24061P2

(12) United States Plant Patent
Graff

(10) Patent No.: US PP24,061 P2
(45) Date of Patent: Dec. 3, 2013

(54) ***HIBISCUS* PLANT NAMED 'LALUNA'**

(50) Latin Name: *Hibiscus rosa-sinensis*
Varietal Denomination: Laluna

(75) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 97 days.

(21) Appl. No.: 13/374,568

(22) Filed: Dec. 31, 2011

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — C. A. Whealy

(57) ABSTRACT

A new and distinct cultivar of *Hibiscus* plant named 'Laluna', characterized by its upright, mounding and bushy plant habit; glossy dark green-colored leaves; uniform and freely flowering habit; double-type orange-colored flowers; and good flower longevity.

3 Drawing Sheets

Botanical designation: *Hibiscus rosa-sinensis*.
Cultivar denomination: 'LALUNA'.

BACKGROUND OF THE INVENTION

The present invention relates to a new and distinct cultivar of *Hibiscus* plant, botanically known as *Hibiscus rosa-sinensis*, and hereinafter referred to by the name 'Laluna'.

The new *Hibiscus* plant is a product of a planned breeding program conducted by the Inventor in Sabro, Denmark. The objective of the breeding program is to create new durable *Hibiscus* plants with attractive double-type flowers with good longevity.

The new *Hibiscus* plant originated from a cross-pollination conducted by the Inventor in December, 2006 in Sabro, Denmark of *Hibiscus rosa-sinensis* 'Calypso Yellow', not patented, as the female, or seed, parent with a proprietary selection of *Hibiscus rosa-sinensis* identified as code number GB 2006-0007, not patented, as the male, or pollen, parent. The new *Hibiscus* plant was discovered and selected by the Inventor as a flowering plant within the progeny of the stated cross-pollination in a controlled greenhouse environment in Sabro, Denmark in September, 2007.

Asexual reproduction of the new *Hibiscus* plant by vegetative terminal cuttings in a controlled greenhouse environment in Sabro, Denmark since October, 2007 has shown that the unique features of this new *Hibiscus* plant are stable and reproduced true to type in successive generations.

SUMMARY OF THE INVENTION

Plants of the new *Hibiscus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Laluna'. These characteristics in combination distinguish 'Laluna' as a new and distinct *Hibiscus* plant:

1. Upright, mounding and bushy plant habit
2. Glossy dark green-colored leaves. .

3. Uniform and freely flowering habit.
4. Double-type orange-colored flowers.
5. Good flower longevity.

Plants of the new *Hibiscus* can be compared to plants of the female parent, 'Calypso Yellow'. Plants of the new *Hibiscus* differ primarily from plants of 'Calypso Yellow' in the following characteristics:

1. Plants of the new *Hibiscus* are more freely branching than plants of 'Calypso Yellow'.
2. Plants of the new *Hibiscus* grow faster than plants of 'Calypso Yellow'.
3. Plants of the new *Hibiscus* have double-type orange-colored flowers whereas 'Calypso Yellow' have single-type yellow-colored flowers.

Plants of the new *Hibiscus* can be compared to plants of the male parent selection. Plants of the new *Hibiscus* differ primarily from plants of the male parent selection in the following characteristics:

1. Plants of the new *Hibiscus* have larger flowers than plants of the male parent selection.
2. Plants of the new *Hibiscus* and the male parent selection differ in flower color as plants of the male parent selection have yellow-colored flowers.
3. Flowers of plants of the new *Hibiscus* last about three days whereas flowers of plants of the male parent selection last one to two days.

Plants of the new *Hibiscus* can be compared to plants of the *Hibiscus rosa-sinensis* 'Classic Red', not patented. In side-by-side comparisons conducted in Sabro, Denmark, plants of the new *Hibiscus* differed from plants of 'Classic Red' in the following characteristics:

1. Plants of the new *Hibiscus* had broader flower buds than plants of 'Classic Red'.
2. Plants of the new *Hibiscus* and 'Classic Red' differed in flower color as plants of 'Classic Red' had pale red-colored flowers.
3. Flowers of plants of the new *Hibiscus* lasted about three days whereas flowers of plants of 'Classic Red' lasted a single day.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of a typical flowering plant of 'Laluna' grown in a container.

The photograph on the second sheet is a close-up view of developing flower buds and an open flower of 'Laluna'.

The photograph on the third sheet is a close-up view of a dissected flower of 'Laluna'.

DETAILED BOTANICAL DESCRIPTION

The aforementioned photographs and following observations, measurements and values describe plants grown during the summer in 13-cm containers in a glass-covered greenhouse in Sabro, Denmark and under environmental conditions and cultural practices which closely approximate commercial *Hibiscus* production. During the production of the plants, day temperatures ranged from 20° C. to 25° C., night temperatures ranged from 19° C. to 21° C. and light levels ranged from 40 to 50 klux. Plants were pinched one time about eight weeks after planting and were 21 weeks old when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Laluna'.

Parentage:

*Female, or seed, parent.*—*Hibiscus rosa-sinensis* 'Calypso Yellow', not patented.

*Male or pollen parent.*—Proprietary selection of *Hibiscus rosa-sinensis* identified as code number GB 2006-0007, not patented.

Propagation:

*Type.*—By vegetative terminal cuttings.

*Time to initiate roots, summer.*—About three weeks at temperatures of 24° C.

*Time to initiate roots, winter.*—About four weeks at temperatures of 24° C.

*Time to produce a rooted young plant, summer.*—About seven weeks at temperatures of 24° C.

*Time to produce a rooted young plant, winter.*—About eight weeks at temperatures of 24° C.

*Root description.*—Medium in thickness, fleshy; color, close to 158A.

*Rooting habit.*—Freely branching; dense.

Plant description:

*Plant and growth habit.*—Upright, mounding and bushy plant habit; moderately vigorous growth habit.

*Branching habit.*—Freely branching habit with usually about six to ten lateral branches developing per plant; pinching enhances lateral branch development.

*Plant height.*—About 35 cm to 55 cm.

*Plant diameter* (*area of spread*).—About 30 cm to 50 cm.

Lateral branch description:

*Length.*—About 15 cm to 25 cm.

*Diameter.*—About 5 mm to 10 mm.

*Internode length.*—About 1 cm to 5 cm.

*Strength.*—Strong.

*Texture.*—Woody.

*Color.*—Close to N199A.

Foliage description:

*Arrangement.*—Alternate, single; numerous; symmetrical.

*Length.*—About 8 cm to 10 cm.

*Width.*—About 4 cm to 7 cm.

*Shape.*—Obovate.

*Apex.*—Acute to cuspidate.

*Base.*—Obtuse.

*Margin.*—Crenate.

*Texture, upper and lower surfaces.*—Smooth, glabrous.

*Luster, upper surface.*—Glossy.

*Luster, lower surface.*—Matte.

*Venation pattern.*—Pinnate; arcuate.

*Color.*—Developing leaves, upper surface: Close to 135A. Developing leaves, lower surface: Close to 143A. Fully expanded leaves, upper surface: Close to N189A; venation, close to 138A. Fully expanded leaves, lower surface: Close to 147A; venation, close to 138B.

*Petiole.*—Length: About 3 cm to 5 cm. Diameter: About 2 mm to 3 mm. Texture, upper and lower surfaces: Pubescent. Color, upper surface: Close to N189A. Color, lower surface: Close to 137A and N199A.

Flower description:

*Flower arrangement.*—Double-type flowers arranged singly at terminal leaf axils; uniform, continuous and freely flowering habit with numerous flower buds and open flowers per plant at one time; flowers face mostly upright to outwardly.

*Fragrance.*—None detected.

*Natural flowering season.*—Plants flower in the garden during the spring and summer or during periods of warm weather; in the greenhouse, plants can be flowered year-round; plants begin flowering about 12 to 14 weeks after pinching.

*Flower longevity.*—Good flower longevity, flowers last for about three days; flowers persistent.

*Flower diameter.*—About 16 cm to 19 cm.

*Flower length* (*height*).—About 7 cm.

*Flower bud.*—Rate of opening: Flowers buds open in about three days. Length: About 4 cm to 6 cm. Diameter: About 3 cm to 5 cm. Shape: Broadly ovate. Color: Close to 31A.

*Petals.*—Arrangement: Corolla consists of about 30 petals that are fused at base; petals imbricate. Length: About 5 cm to 10 cm. Width: About 4 cm to 8 cm. Shape: Fan-shaped. Apex: Rounded. Base: Attenuate. Margin: Entire, undulate. Texture, upper surface: Glabrous; rugose; velvety. Texture, lower surface: Glabrous; rugose; satiny. Color: When opening, upper surface: Close to N25A; towards the base, close to 46A. When opening, lower surface: Close to 31A. Fully opened, upper surface: Close to 28B; towards the base, close to 46A; color does not fade with development. Fully opened, lower surface: Close to 31B.

*Sepals.*—Appearance: Five sepals fused into a tubular star-shaped calyx. Length: About 3 cm. Width: About 1.2 cm. Shape: Lanceolate. Apex: Acuminate. Margin: Entire. Texture, upper surface: Rough. Texture, lower surface: Smooth. Color, upper surface: Close to 143A. Color, lower surface: Close to 144B.

*Peduncles.*—Length: About 3 cm to 5 cm. Diameter: About 2 mm to 3 mm. Strength: Strong. Texture: Pubescent. Color: Close to 146A.

*Reproductive organs*.—Androecium: Stamen number: None to about 100. Filament length: About 1 mm to 2 mm. Filament color: Close to 25C. Anther shape: Rounded to ovate. Anther length: About 1 mm to 2 mm. Anther color: Close to 19A. Amount of pollen: None to abundant. Pollen color: Close to 17B. Gynoecium: Pistil length: About 7 cm to 8 cm. Style length: About 6 cm. Style texture: Smooth, waxy. Style color: Close to 11D; towards the base, close to 53A. Stigma appearance: Five-parted, rounded. Stigma color: Close to N30A. Ovary color: Close to 145A.

*Seeds*.—Quantity produced per flower: About one to ten. Length: About 3 mm. Diameter: About 3 mm. Color: Close to 202A.

Temperature tolerance: Plants of the new *Hibiscus* have been observed to have tolerate temperatures from about 1° C. to about 35° C.

Pathogen & pest resistance: Plants of the new *Hibiscus* have not been observed to be resistant to pathogens and pests common to *Hibiscus*.

It is claimed:

1. A new and distinct *Hibiscus* plant named 'Laluna' as illustrated and described.

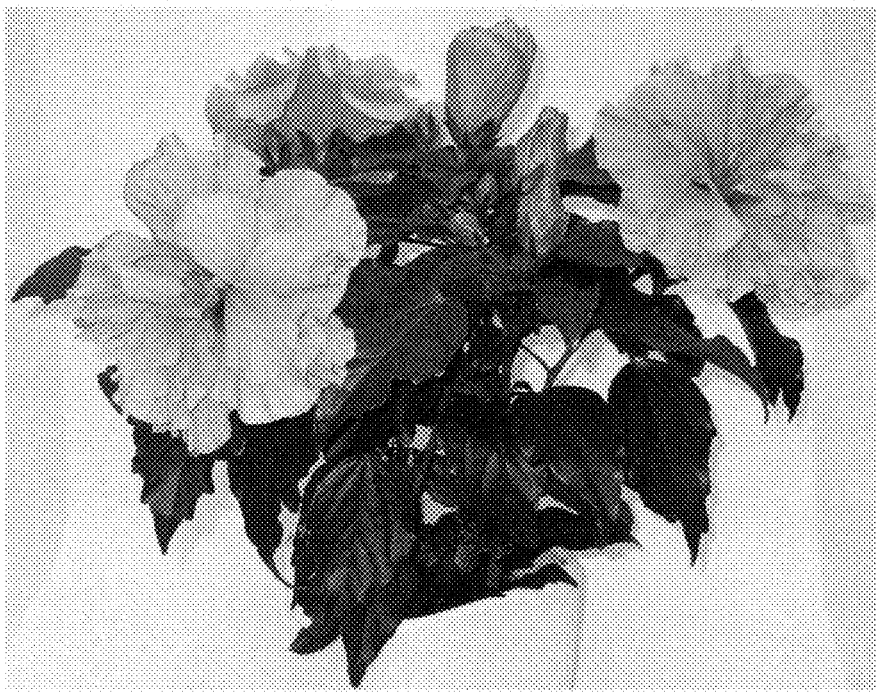

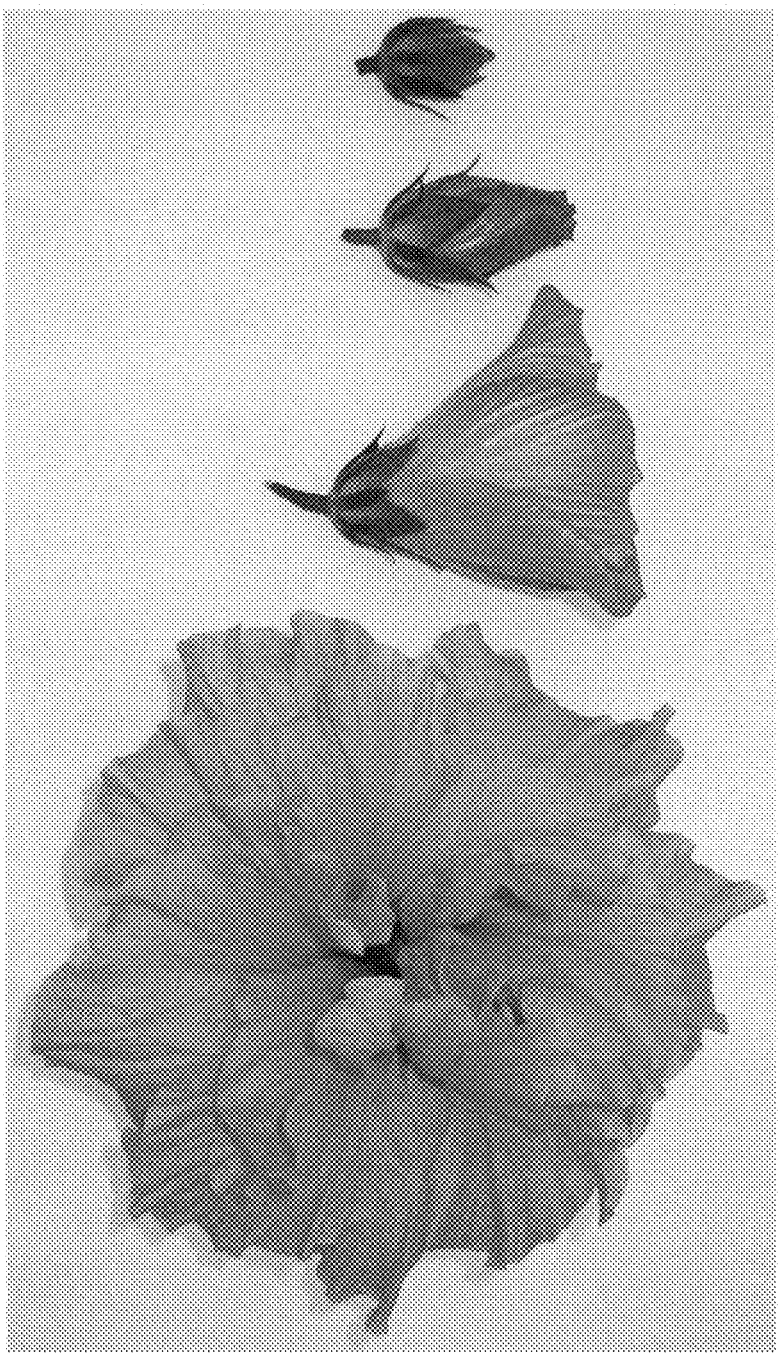

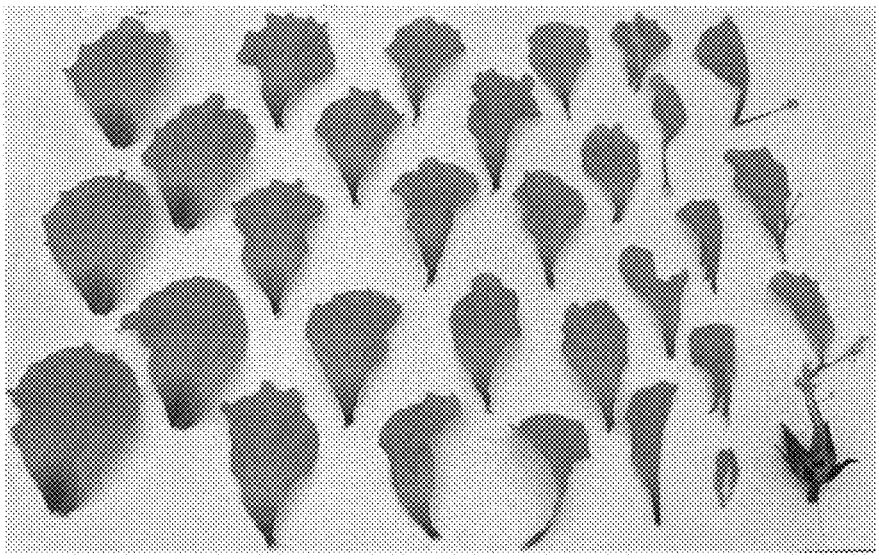

* * * * *